United States Patent [19]
Kertz

[11] Patent Number: 5,511,340
[45] Date of Patent: Apr. 30, 1996

[54] PLANT GROWING ROOM

[76] Inventor: Malcolm G. Kertz, P.O. Box 426, Bridge City, Tex. 77611

[21] Appl. No.: 943,264

[22] Filed: Sep. 10, 1992

Related U.S. Application Data

[63] Continuation-in-part of Ser. No. 777,479, Oct. 17, 1991, Pat. No. 5,166,870, and a continuation-in-part of Ser. No. 672,736, Mar. 21, 1991, Pat. No. 5,171,683, which is a continuation of Ser. No. 207,405, Jun. 14, 1988, abandoned, which is a continuation-in-part of Ser. No. 21,408, Mar. 4, 1987, Pat. No. 4,908,315, said Ser. No. 777,479, is a division of Ser. No. 365,585, Jun. 13, 1989, abandoned, which is a continuation-in-part of Ser. No. 207,405, which is a continuation-in-part of Ser. No. 21,408.

[51] Int. Cl.⁶ ..................................................... A01G 31/02
[52] U.S. Cl. ....................... 47/65; 47/82; 47/83
[58] Field of Search ............................ 47/17 MS, 65 D, 47/65 F, 65 M, 39 M, 66

[56] References Cited

U.S. PATENT DOCUMENTS

| Des. 140,519 | 3/1945 | Pascal | 383/39 |
|---|---|---|---|
| 1,914,967 | 6/1933 | Bebb | 211/71 |
| 3,160,986 | 12/1964 | Watson et al. | 47/56 |
| 3,172,234 | 3/1965 | Eavis | 47/1.2 |
| 3,207,421 | 9/1965 | Hanger | 383/39 |
| 3,384,993 | 5/1968 | Kane | 47/58 |
| 3,568,853 | 3/1971 | Feibelman | 211/113 |
| 3,613,309 | 10/1971 | Coburn | 47/38 |
| 3,739,522 | 6/1973 | Greenbaum | 47/34.13 |

(List continued on next page.)

FOREIGN PATENT DOCUMENTS

| 241191 | 11/1964 | Austria | 47/65 D |
|---|---|---|---|
| 0031985 | 7/1981 | European Pat. Off. . | |
| 0042697 | 12/1981 | European Pat. Off. . | |
| 0282230 | 9/1988 | European Pat. Off. . | |
| 1475610 | 2/1967 | France | 47/17 MS |
| 2621448 | 4/1989 | France | 47/17 EC |
| 3634805 | 4/1988 | Germany | 47/65 D |
| 8401090 | 11/1985 | Netherlands | 47/65 D |
| 8402614 | 3/1986 | Netherlands | 47/65 D |
| 1034218 | 12/1985 | U.S.S.R. | 47/65 D |
| 714638 | 9/1954 | United Kingdom | 47/17 EC |
| 1457920 | 12/1976 | United Kingdom | 47/65 D |
| WO8705885 | 8/1987 | WIPO . | |
| WO8806402 | 9/1988 | WIPO . | |

OTHER PUBLICATIONS

Chevron Chemical Co.; *Chevrol Polyethylene Resins for Extrusion;* (8 pgs.).
Chevron Chemical Co.; Technical Data Sheet; *High Density Polyethylene Blow Molding Resin;* HiD 9506; (2 pg.).
Chevron Chemical Co.; Technical Data Sheet; *High Density Polyethylene Blown Film Resin;* HiD9650; (2 pg.).
Chevron Chemical Co.; Technical Data Sheet; *Low Density Polyethylene High Clarity, High Impact Film Resin for General Purpose Packaging;* PE 5754; (2 pg.).
Biotechnology Letters, vol. 7, No. 7; pp. 467–470 (1985) *A Device for Cultivation of Plant and Animal Cells;* Jan Kybal, and Bohumil Sikytra.
Modern Plastics, vol. 34, Sep. 1956; *Film on the Farm;* (13 pgs.).
Horticulture; vol. XXXI, Sep. 1953; *Gardening with Plastics;* George Taloumis.
Acta Horticulturae 178, 1986 *Vertical Bag System Used for Mother Foliage Pot Plants Culture, Effects of Substrates;* pp. 245–256.

Primary Examiner—Henry E. Raduazo
Attorney, Agent, or Firm—Conley, Rose & Tayon

[57] ABSTRACT

The growing room includes a closed loop track suspended above the floor and extending throughout the room. A plurality of racks are movably supported on the track by a motorized mover system. The racks include a frame for supporting a plurality of growing sheets for supporting and growing the plants. The growing sheets are made of a translucent material and include a plurality of growing cells formed by affixing a plurality of lengths of membrane material to the sheet at predetermined locations. The growing cells are gas permeable, liquid impermeable, and translucent.

16 Claims, 4 Drawing Sheets

U.S. PATENT DOCUMENTS

| | | | |
|---|---|---|---|
| 3,749,237 | 7/1973 | Dorton | 383/39 |
| 3,924,781 | 12/1975 | Witte | 248/95 |
| 4,034,508 | 7/1977 | Dedolph | 47/84 |
| 4,075,785 | 2/1978 | Jones | 47/64 |
| 4,251,951 | 2/1981 | Heinstedt | 47/39 |
| 4,255,897 | 3/1981 | Buthner | 47/65 D |
| 4,311,477 | 1/1982 | Kitamura et al. | |
| 4,316,347 | 2/1982 | Smith | 47/17 R |
| 4,356,664 | 11/1982 | Ruthner | 47/17 MS |
| 4,424,645 | 1/1984 | Rannali | 47/66 |
| 4,629,070 | 12/1986 | Roberg | 383/39 |
| 4,908,315 | 3/1999 | Kertz | 435/240 |
| 4,911,777 | 3/1977 | True | 383/39 |
| 4,938,368 | 7/1990 | sharman | 211/71 |
| 4,965,967 | 10/1990 | Akagi | 47/65 D |
| 5,171,683 | 12/1992 | Kertz | 435/240 |

PLANT GROWING ROOM

RELATED APPLICATIONS

This application is a continuation-in-part of U.S. application Ser. No. 07/777,479 filed Oct. 17, 1991 and now abandoned, which is a continuation of U.S. application Ser. No. 07/365,585 filed Jun. 13, 1989 and now abandoned, which is a continuation-in-part of U.S. application Ser. No. 07/207,405 filed Jun. 14, 1988 and now abandoned which is a continuation-in-part of U.S. application Ser. No. 07/021,408 filed Mar. 4, 1987 and now U.S. Pat. No. 4,908,315 issued Mar. 13, 1990. This application is also a continuation-in-part of U.S. application Ser. No. 07/672,736 filed Mar. 21, 1991 and now U.S. Pat. No. 5,171,683, which is a continuation in part of U.S. application Ser. No. 07/207,405 filed Jun. 14, 1988 and now abandoned which is a continuation-in-part of Ser. No. 07/21,408 now U.S. Pat. No. 4,908,315 issued Mar. 13, 1990.

FIELD OF THE INVENTION

The present invention relates to a new and improved growing room and more particularly to an automated greenhouse for growing plantlets.

BACKGROUND OF THE INVENTION

Seeds and plantlets are individually planted in a soil medium and housed in a greenhouse for germination and hardening. During this process, the seeds or plantlets are planted in a soil medium contained in small plastic liners which are placed in a flat. These flats are then stored in the greenhouse, often on wooden supports such as tables or benches on the greenhouse floor. The plantlets are typically placed side by side at a common elevation in the greenhouse to form a mat of plants extending across the greenhouse on a common plane. By placing the plantlets together as described in the prior art, the plantlets tend to reduce the light that is available to adjacent plants and also cause dead air spaces adjacent the plants, thus inhibiting growth. Further, the liners, flats or pots are opaque and therefore do not transmit any available light therethrough.

A further disadvantage of prior art systems is that the liners must be manually moved from one location to another. In particular, to remove plantlets from the liners, the liners either need to be removed from the greenhouse or the laborer must work at the location of the liner.

Other objects and advantages of the invention will appear from the following description.

SUMMARY OF THE INVENTION

The present invention includes an automatic growing room. The growing room includes a closed loop track suspended above the floor and extending throughout the room. A plurality of racks are movably supported on the track by a motorized mover system. The racks include a frame for supporting a plurality of growing sheets for supporting and growing the plants. The growing sheets are made of a translucent material and include a plurality of growing cells formed by affixing a plurality of lengths of membrane material to the sheet at predetermined locations. The growing cells are gas permeable, liquid impermeable, and translucent.

BRIEF DESCRIPTION OF THE DRAWINGS

For a detailed description of the preferred embodiment of the invention, reference will now be made to the accompanying drawings, wherein.

DESCRIPTION OF THE PREFERRED EMBODIMENT

Figure 1:
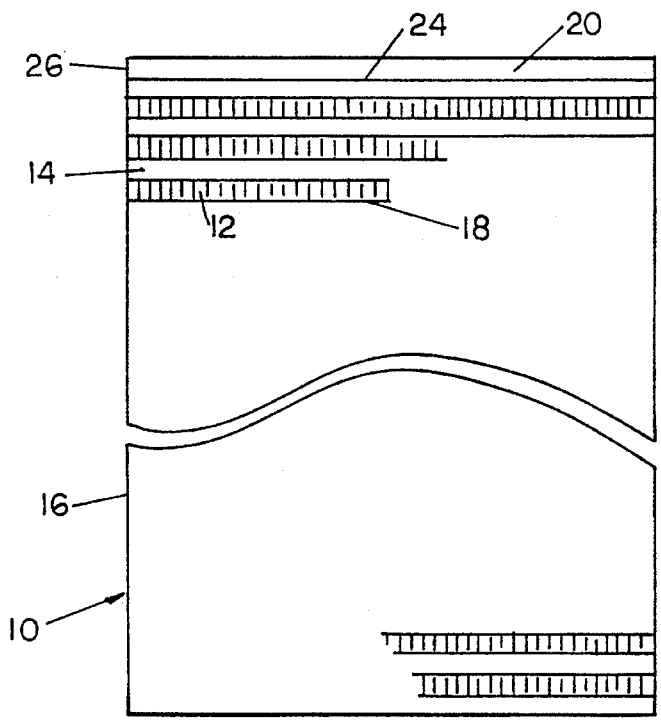
FIG. 1 is an elevation view of the growing sheet of the present invention.

Referring initially to FIG. 1, there is shown a growing sheet 10 made of a support material 16 having attached thereto a plurality of lengths of membrane material 18 affixed to support material 16 at predetermined locations to form a plurality of horizontal rows of growing cells 12. The rows of growing cells 12 are separated by horizontal growing spaces 14. Growing cells 12 are adapted to grow and support plants to be grown within cells 12. The growing cell 12 provides the root zone for the plant and the growing space 14 provides the foliage area for the plant as the plant grows. Attachment means 20 is provided at the top of growing sheet 10 for supporting the growing sheet 10 on a frame 22 shown in FIG. 5. The attachment means 20 includes folding over the upper edge of support material 16 and heat sealing the adjacent sheets together at 24 to form an elongated loop 26 for receiving a portion of the frame 22 as hereinafter described.

The growing sheet 10 is sized to accommodate the variety of plants being grown in the growing cells 12 and for ease in material handling. The growing cells 12, illustrated in FIG. 1, are used primarily for seed germination and production. In such an application, one preferred size of growing sheet 10 is a growing sheet 2 feet wide and 3 feet high. Growing cells 12 for seed germination and production are approximately ¼ inch in diameter and ½ inch to 1 inch high. The horizontal growing spaces 14 preferably have a height approximately the same as that of the growing cells 12, i.e. ½ inch to 1 inch high. Growing sheets having dimensions greater than 2 feet by 3 feet cause a material handling problem due to the physical size of the growing sheet and weight of the seeds and growth media, such as soil, in the growing cells 12. A growing sheet 10 with the preferred size of 2 feet by 3 feet would accommodate approximately 35 rows of cells with approximately 175 cells per row thus, each growing sheet would accommodate approximately 6125 growing cells. However, as discussed previously, the capacity of the growing sheet 10 will vary substantially depending upon the stage of plant production and the size and variety of the seed or plantlet.

Each growing cell 12 provides a container or pouch for maintaining the growing media and plant material. Typically, the plant material may include seeds, cuttings, plant tissue, or plantlets. The growing media is typically soil but may be other types of growing media such as growing foam. The growing medium of soil is typically a peat moss-based mix with a controlled pH. The soil is blown, dropped or pushed into the pouch and then wetted. Additional soil is blown, dropped or pushed into the cell until the growing cell 12 is filled with the growing media. A plant material is then planted into the soil. Typical applications of the growing cells for seed germination include germination of petunia, marigold, and pansy seeds. The planting of root cuttings might include azaleas and African violets. A typical tissue cutting planted in the soil might be a syngonium (Devil's Point Ivy).

After a predetermined amount of foliage has grown from the growing cell 12 adjacent the foliage area 14, the plug is removed from the growing cell and transplanted into a larger growing cell of another growing sheet 10. Obviously, larger cuttings or larger plants require larger growing cells 12. Also, the growing cells 12 may be indexed so that an automatic seeder may be used to plant the seeds into the growing cells 12.

Figure 4:
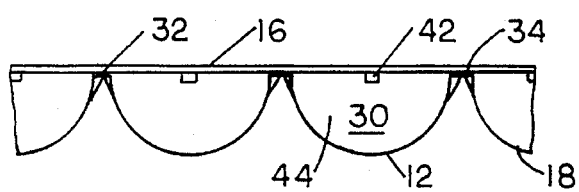
FIG. 4 is a top view of the growing cells shown in FIG. 2.
Figure 2:
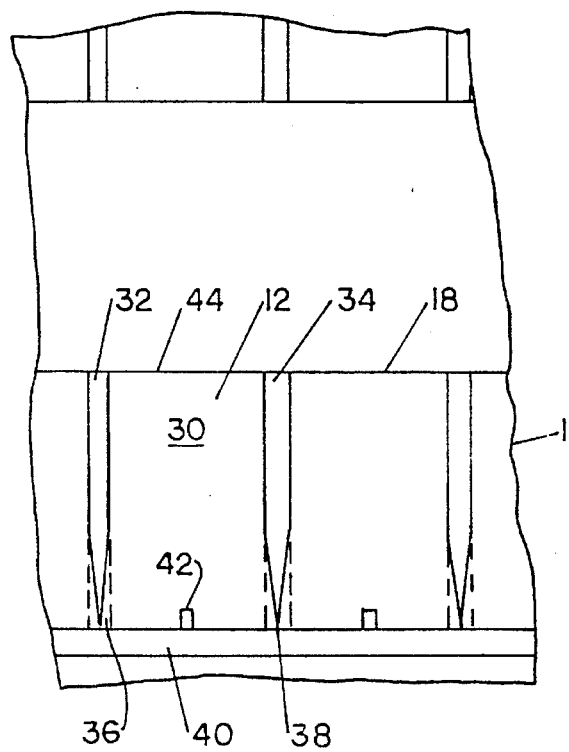
FIG. 2 is an enlarged view of a portion of the growing sheet of FIG. 1 illustrating individual growing cells of the present invention.
Figure 3:
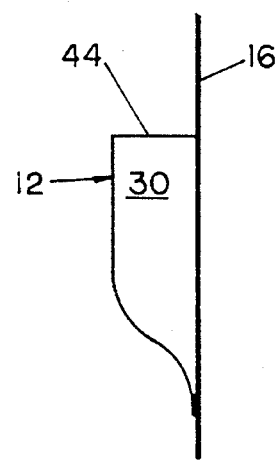
FIG. 3 is a side view of the growing cell shown in FIG. 2.

Referring now to FIGS. 2–4, each growing cell 12 forms a container or pouch 30 for containing the growing media and plant material. The growing cells 12 are formed by heat sealing the length of membrane material 18 at predetermined vertical locations 32, 34 to form a generally semi-circular cross-sectional area through the growing cell 12. The billowing of the open end 44 causes the growing cell 12 to always be in the open and receiving position for the insertion of the growing media and plant material. The bottom of the growing cell 12 is folded against the support sheet 16 such that the excess material at 36, 38 is evenly folded outward with the lower edge of growing cell 12 being heat sealed at 40. The folding of the lower edge of growing cell 12 is important because other folding patterns may well cause the opening 44 of growing cell 12 to be unduly restricted or completely collapsed so as to make it extremely difficult to introduce growing media into the pouch 30. A puncture or slit is provided at the bottom of growing cell 12 to form a drainage or weep hole 42 to allow excess water to drain from pouch 30.

Figure 11:
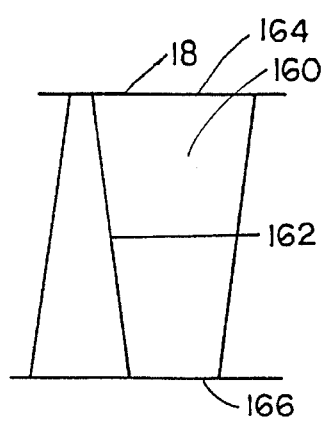
FIG. 11 is an alternative embodiment of the growing cell shown in FIG. 2 of the present invention.

FIG. 11 illustrates an alternative embodiment of the growing cell. Growing cell 160 is formed by heat sealing the length of membrane material 18 at a 10 degree angle with vertical, such as at 162, to form a cross-sectional area in the shape of a truncated cone. The upper end 164 is open for receiving the growing media and plant material. The bottom 166 of growing cell 160 may be heat sealed or reduced in size or restricted so as to be open but prevent the growing media from escaping from within growing cell 160. By allowing the bottom 166 to be open, upon completed growth, the plant may be popped out of cell 160 by pushing the plant and growing media from the bottom by accessing the opening at bottom 166 of cell 160. An open bottom also allows drainage of excess moisture from the pouch formed by cell 160.

The support material 16 and membrane material 18 are preferably made of high-density polyethylene film and more preferably Chevron HiD 9650. Chevron HiD 9650 is described in U.S. Pat. No. 4,908,315 dated Mar. 13, 1990, U.S. patent application Ser. No. 07/207,405 filed Jun. 14, 1988, and U.S. patent application Ser. No. 07/365,585 filed Jun. 13, 1989, all of which are incorporated herein by reference. The support material 16 and membrane material 18 may have varying film thicknesses but are preferably 1.25 mils. It is also preferred that the support material 16 and membrane material 18 be a starch-loaded film and thus degradable. It is preferred that the film degrade in a relatively short period of time. Thus, a reground or recyclable polyethylene might also be used. Since the gas exchange rate at the root zone is important, a low density polyethylene with a greater gas exchange rate might be used in place of high density polyethylene for the membrane material 18. Such a low density polyethylene would have a greater thickness such as 2.0 mils. Low density polyethylene also has the advantage in that it is cheaper than high density polyethylene.

The support material 16 and membrane material 18 are gas permeable, liquid impermeable, and translucent. A greater growth rate is achieved at the root zone if the gas exchange rate through material 16, 18 is high. Although the weep hole 42 allows the release of excess water, the material 16, 18 are liquid impermeable to hold and maintain the moisture in the growing medium. Also, the material 16, 18 are translucent to allow light to reach the root zone but, more importantly, to allow the light to pass through adjacent growing sheets 10 to reach plant material at various heights and locations within the growing enclosure 100, hereinafter described.

The weep hole 42 only need be small enough so that the growing medium will not pass through the bottom of growing cell 12. A larger weep hole 42 has the advantage of permitting the plug to be removed by pushing the plug of soil and plant material up through the open end 44 of growing cell 12 by pushing from the bottom through the weep hole 42.

Certain variations may be made to the growing cell 12 to accommodate particular types of plants. For example, the membrane material 18 forming the outer shell of the growing cell 12 may be of a thinner plastic film to achieve greater gas exchange. Little structural support is required by the membrane material 18 and thus a thinner material produces a reduction in cost. Also, the support material 16 and/or the membrane material 18 may be opaque to maintain the root zone of particular plants within an opaque enclosure.

Figure 5:
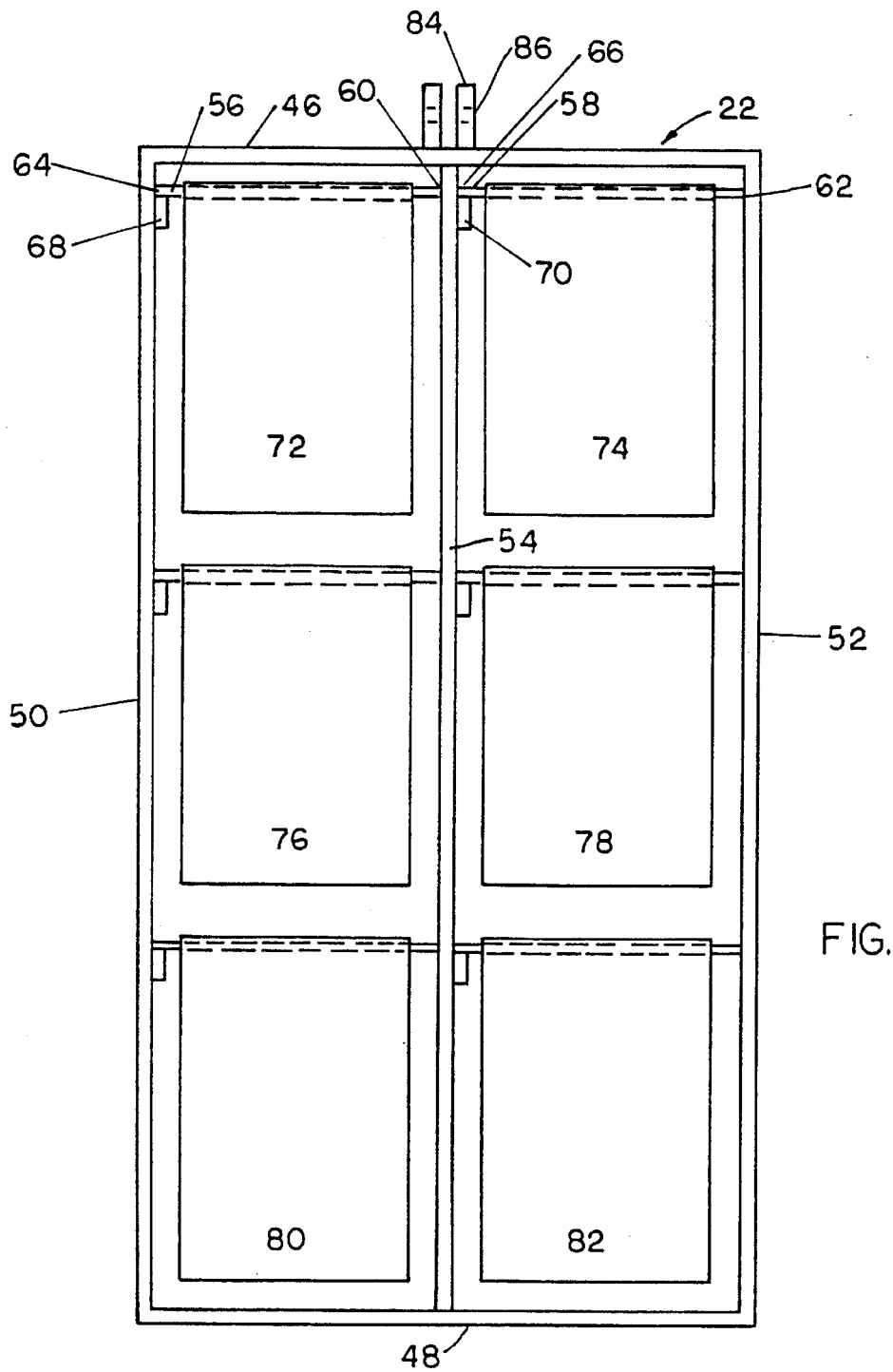
FIG. 5 is an elevation view of a plurality of growing sheets suspended from a frame of the present invention.

Referring now to FIG. 5, frame 22 is a generally rectangular rigid member preferably made of metal such as angle iron. Although frame 22 may vary in dimension, it is preferred that frame 22 have a width of approximately 5 feet and a height of approximately 10 feet. Frame 22 includes a top bar 46, a bottom bar 48, two side bars 50, 52 and a center bar 54. Frame 22 further includes three pairs of support rods 56, 58. Support rods 56, 58 are hinged at one end 60, 62 and are supported at the other end 64, 66 by support hooks 68, 70. A clevis 84 is mounted at the center of top bar 46 of frame 22 for attachment to a track 90 hereinafter described with respect to FIG. 8. For an alternative frame, see FIGS. 15 and 16 of U.S. Pat. No. 4,908,315 incorporated herein by reference.

As illustrated in FIG. 5, six growing sheets 72, 74, 76, 78, 80, and 82 are supported by the three pairs of support rods 56, 58 on frame 22. To support growing sheets 72–82 on rods 56, 58, support rods 56, 58 are unlatched from hooks 68, 70 and swung outward on hinges 60, 62 so that rods 56, 58 may be received by loop 26 at the top of the growing sheets 72–82. After support rods 56, 58 are inserted in loop 26, the ends of rods 56, 58 are again latched to hooks 68, 70. The lower free ends of growing sheets 72– 82 are allowed to sway or swing on support rods 56, 58. The three pairs of support rods 56, 58 are located on frame 22 such that growing sheets 72–82 clear side bars 50, 52 and center bar 54 by a few inches on each side thereof and the bottom of growing sheets 72–82 are from 5 to 6 inches above any lower and adjacent growing sheet-such as growing sheets 76, 78 and 80, 82.

Figure 6:
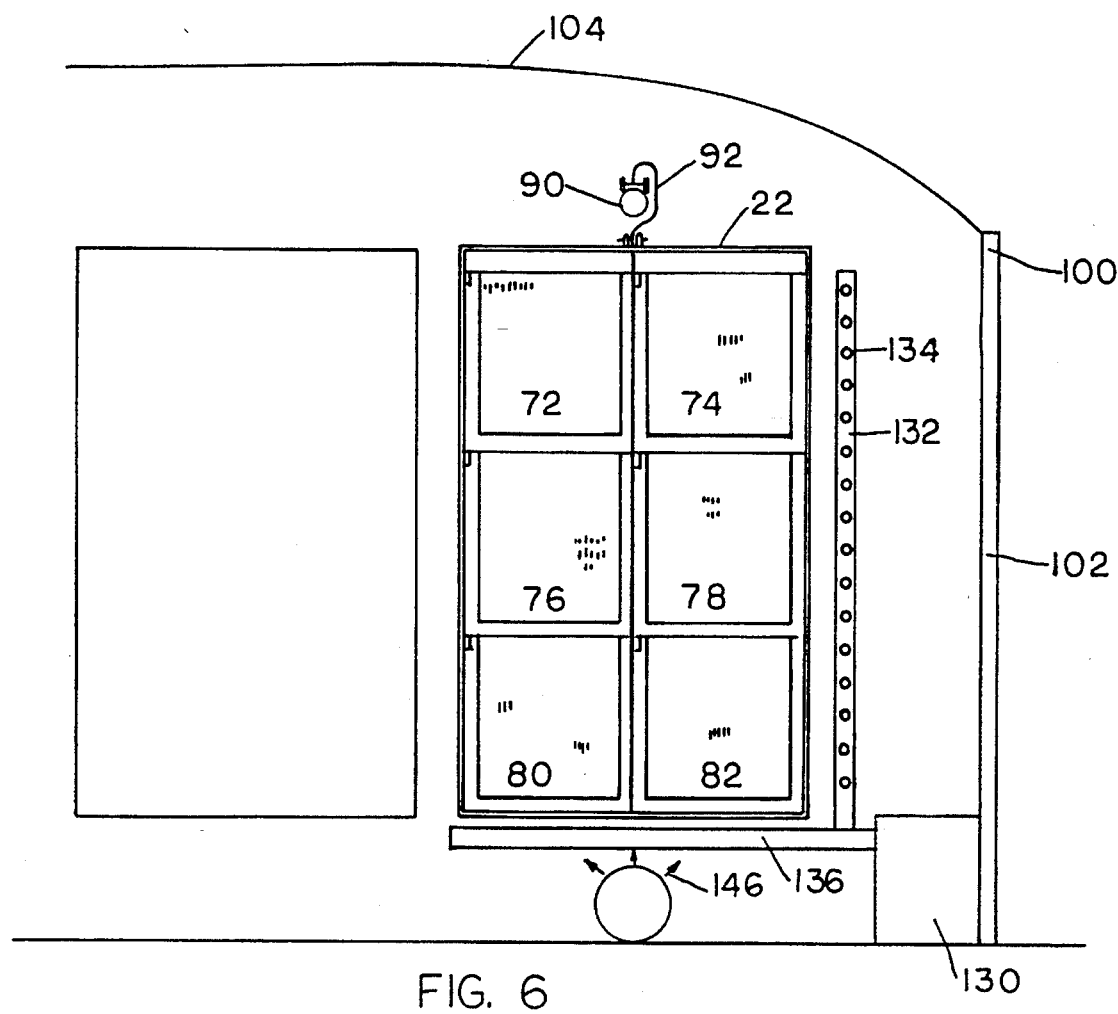
FIG. 6 is a cross-sectional view of the growing room of the present invention illustrating a rack with growing sheets mounted within the growing room.
Figure 7:
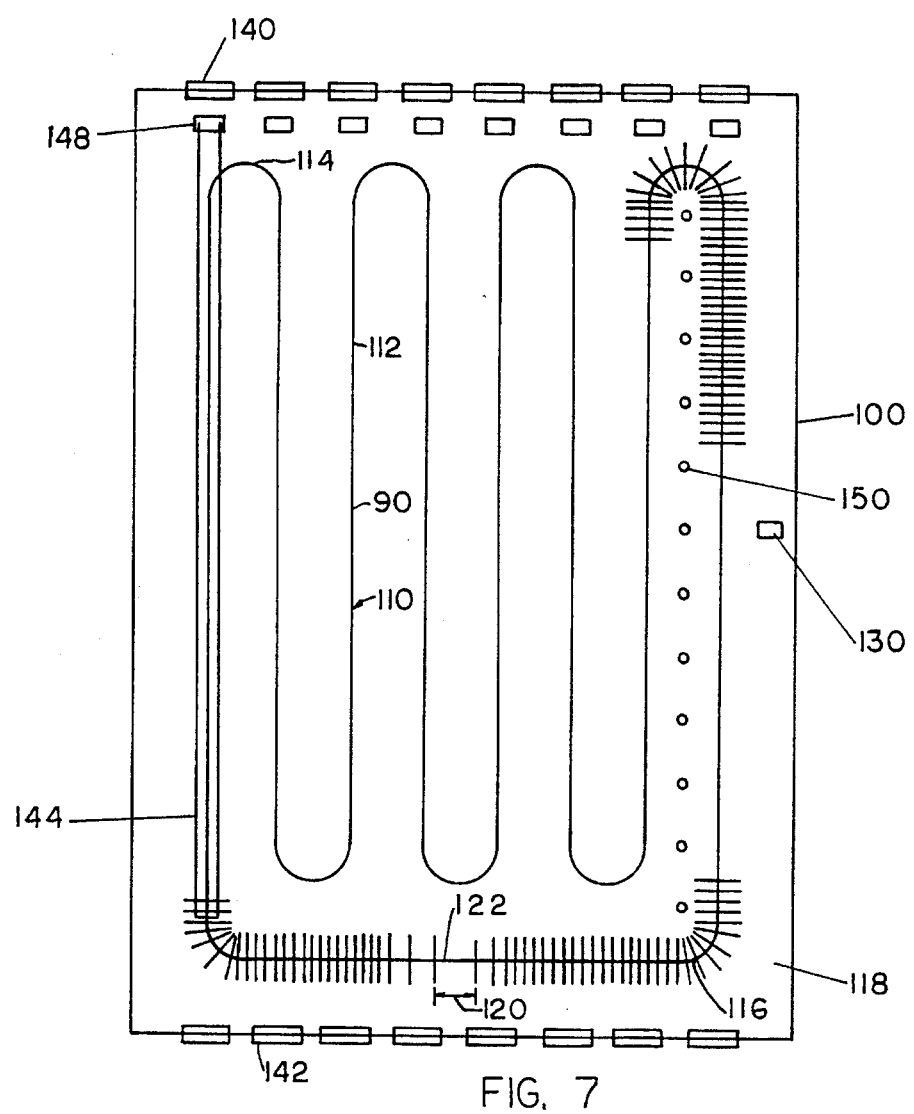
FIG. 7 is a schematic top view of the growing room having a plurality of racks with growing sheets suspended within the growing room on a track of the present invention.

Referring now to FIGS. 6 and 7, growing sheets 10 and frames 22 with growing media and plant material are housed in an enclosure or growing room 100. Growing room 100 may be a greenhouse using ambient light or an enclosed structure such as a warehouse with artificial lighting as hereinafter described. Further, the size of the growing room 100 may vary. A typical greenhouse is shown in FIGS. 6 and 7 as growing room 100. For purposes of illustration, the growing room shown in FIGS. 6 and 7 is approximately 40 feet wide and has a length or run of approximately 100 feet. The vertical walls 102 forming the perimeter of the growing room 100 are shown to be 12 feet high with an arching roof 104 having a height of approximately 18 feet at its peak. The roof 104 may be made of various materials which allow the passage of ambient light. The floor may be the ground or made of any well known construction material. See also the disclosure of U.S. Pat. No. 4,978,505 incorporated herein by reference.

The growing room 100 of the present invention includes a closed loop 110 of track 90. As illustrated in FIG. 7, closed loop 110 may have a serpentine pattern within growing room 110. With the growing room dimensions as described, loop 110 may include eight rows of track 112 having a plurality of U-turn loops 114 attaching adjacent track rows and an end loop 116. End loop 116 passes through a head end 118 of growing room 100. Head end 118 is typically the working area of growing room 100 for the planting and handling of the growing media and plant material in growing sheets 10.

Figure 8:
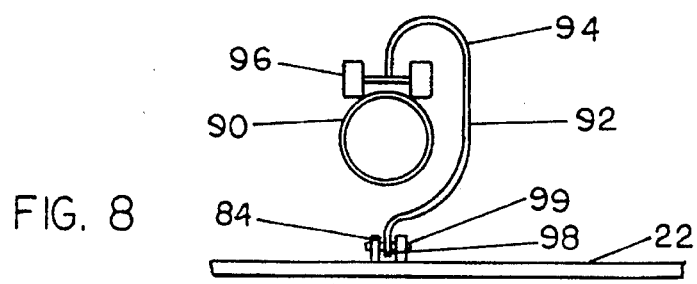
FIG. 8 is an elevation view of the support mechanism for the rack suspended from the track of the present invention.

Referring particularly to FIG. 6, each frame 22 with growing sheets 72–82 is suspended from track 90 by a support mechanism 92. As shown in FIG. 8, track 90 is a tubular pipe supported within growing room 100 in the serpentine fashion shown in FIG. 7. Support mechanism 92 includes a generally C-shaped support member 94 having a pair of rollers 96 on one end and another end 98 received by clevis 84 of rack 22. Rack 22 is mounted on support mechanism 92 by a pin 99 passing through aligned apertures 86 and clevis 84 and support member 94.

As shown in FIG. 7, a plurality of racks supporting a plurality of growing sheets 10 are suspended from the serpentine track 90 within growing room 100. A motorized mover system, not shown, similar to conveyor Model N-610-L manufactured by White Conveyor, Inc. of Kenilworth, N.J. or conveyor Model EU-920 of Saratoga Conveyor of Lithian Springs, Ga., manufactured by K. P. Fabrication, Inc., is provided in growing room 100 to move racks 22 with growing sheets 10 through the growing room 100. Such is shown schematically in FIG. 7. Adjacent racks 22 are spaced from each other by spacers, not shown, mounted on mechanism 92 for contacting the mechanisms 92 of adjacent racks 22. The length of these spacers can be varied to vary the distance between adjacent racks. Preferably, the racks are maintained a matter of inches, such as 2 to 3 inches apart so as to maximize the capacity of growing room 100 to house the growing plants. The clearance between racks is preferably 4 to 6 inches. Although a single track 90 is shown, a multiple track may be used. A single track has the advantage that no alignment is required.

The racks 22 with growing sheets 10 are propelled along track 90 at a rate preferably less than 1 foot per second and preferably approximately 10 feet per minute. This movement throughout the growing room 100 permits the plant material of an individual growing sheet 10 to pass through all of the zones of the growing room 100. The temperature, humidity and lighting in a given area or zone of the growing room 100 may vary from another. Movement of the racks 22 and growing sheets 10 through the growing room 100 permits a more even growth of all plant material. Further, the movement of the growing sheets 10 through the room 100 has the additional affect of creating air movement. As the racks 22 and growing sheets 10 move through growing room 100, the growing sheets 10 sway on racks 22 causing an air movement. The growing sheets 10, therefore, act as paddles against the air causing a mixing pattern of air movement throughout the growing room 100.

Figure 9:
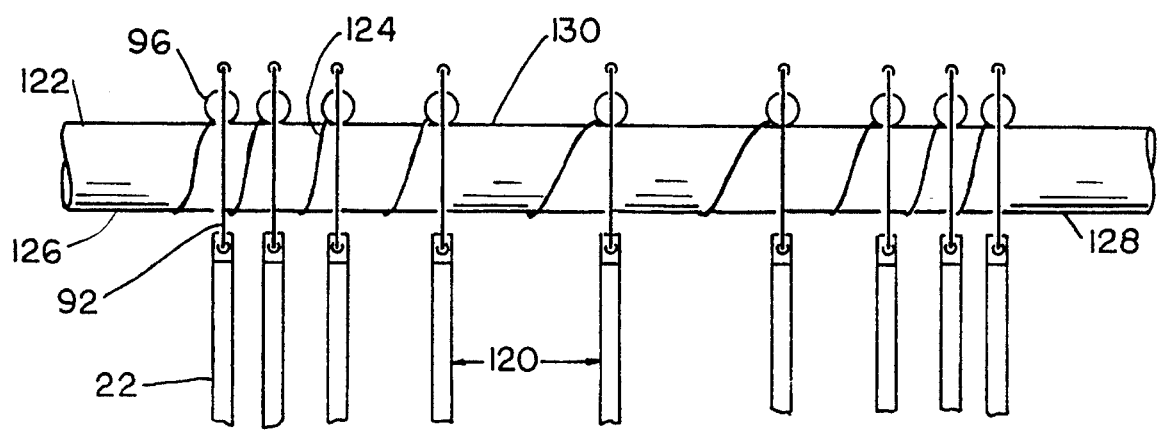
FIG. 9 is an elevation view of the screw section of the track of the present invention.

Referring now to FIG. 9, it is necessary at the head end 118 of growing room 100 to expand the distance 120 between adjacent racks 22 so that workers may have better access to individual growing cells 12 on a particular growing sheet 10. To provide this expanded distance 120, track 90 includes a screw section 122 having a thread 124 extending spirally around the track. The spiraling threads 124 of screw section 122 are closer together at the ends 126, 128 of pipe section 122 and are further apart at the midportion 131 of section 122. As the racks 22 move onto screw section 122, the rollers 96 are engaged by spiraling thread 124. As the spaces between adjacent threads 124 becomes greater near midportion 130, adjacent racks 22 become separated a greater distance 120. The motorized system can be stopped at any time to then allow a worker to pass between adjacent racks 22 and have access to individual growing sheets 10 and growing cells 12.

Referring again to FIGS. 6 and 7, one or more misters 130, such as Model Maximiser manufactured by Canaan Industries, Inc., of Dothan, Ala., are provided at spaced intervals along track 90 for misting the growing plant material as the motorized system moves the racks 22 and growing sheets 10 through the growing room 100. Mister 130 includes a wand 132 with a plurality of misting nozzles 134. Wand 132 is mounted on a track 136 extending below a row of racks 22. The speed of the moving racks is such as to allow the wand 132 to travel between adjacent racks 22 and mist the plants growing on individual growing sheets 72–82. The wand 132 will mist one rack of growing sheets 10 as it travels to the end of track 136 and then mists another rack of passing sheets as it moves back to the other end of track 136. Thus, wand 132 will mist two racks of growing sheets in its full cycle of moving out and back on track 136 of mister 130.

The solution of the mister 130 will depend upon the plant variety as well as the climate of the ambient environment of growing room 100. The solution applied by mister 130 may include various additives such as fertilizer, fungicides, and insecticides. An injection feed system, well known in the art, meters these additives into the water which is then applied to the growing sheets 10 by the passing wand 132. The solution is sprayed onto the support sheet 16 of growing sheet 10 and is allowed to run down the face of support sheet 16 and into the growing cells 12. Excess solution will run and drip onto the floor of the growing room 100 to be collected in a catch basin either to be recycled or disposed.

Figure 10:
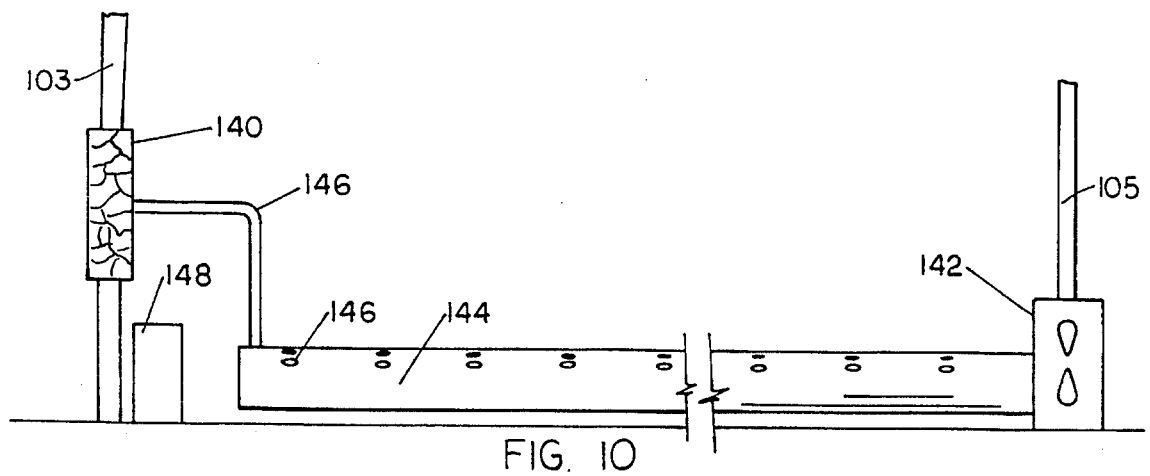
FIG. 10 is a partial elevation view of the interior of the growing room illustrating the heating and cooling system.

Referring now to FIGS. 6, 7 and 10, the present invention includes means for providing air movement within the growing room 100 at a preferred rate and temperature. The growing room 100 includes cooling pads 140 mounted on one end wall 103 of growing room 100. A plurality of exhaust fans 142 are mounted in the opposite end wall 105 of growing room 100. A flexible air conduit 144 extends the length of growing room 100 between cooling pads 140 and exhaust fans 142. A deflector shield 147 is provided on the interior side of cooling pad 140 to direct the fresh cool air through the cooling pad 140 and into the open end of tube 144. The exhaust fan 142 connects with the other end and pulls the air from the cooling pad 140 through the tube 144 and exits the growing room 100. Tube 144 includes a plurality of apertures 146 directed to a particular row of racks 22 and growing sheets 10 so as to blow cooled air onto the plant material. It is preferable that the air movement is approximately 100 feet per minute such that the air within the growing room 100 is exchanged once very minute. The purpose of the fresh air is to kill any anaerobic fungus on the plant material.

During the winter months, the exterior shutters, not shown, on the cooling pads 140 and the tubes 144 are affixed to heaters 148 which blow hot air through tubes 144 and out apertures 146 to heat the plant material.

The growing room 100 may further provide a fogging system, such as the System 1000 MicroMist System manufactured by Baumac International of Mentone, Calif., mounted in the ceiling thereof to maintain the humidity levels within the growing room 100 to approximately 80% or more. The fog is permitted to filter down between the racks 22 to maintain the humidity of the seedlings.

Where the growing room 100 is a greenhouse, the ambient light will be sufficient to provide the necessary lighting for the plant material. The movement of the racks 22 and growing sheets 10 through the growing room 100 will also insure that the plant material has sufficient light. It is also possible that the individual growing sheets 72–82 may be rotated on rack 22 to insure that the plant material on the lower sheets 80, 82 receive as much light as those on the upper growing sheets 72, 74.

Where the growing room 100 is an enclosed structure such as a warehouse, artificial lighting will be provided along the ceiling and floor. Further, the interior of the growing room 100 would be painted a reflective color, such as white or aluminum. If necessary, a plurality of floor lights 150 may be disposed between adjacent tracks of racks 22 as shown in FIG. 7 to provide additional light. Where lights 150 are provided, such lighting would also become a primary heat source thereby reducing the need for heaters 148.

In the prior art, approximately 648 plugs are planted per tray. Each tray is approximately 11 inches by 22 inches. However, the trays are opaque and do not permit the passage of light. Thus, only one level of trays can be used throughout the greenhouse. This only allows approximately 400 plugs per square foot of growing room. However, the present invention includes approximately 5400 plants per rack, i.e. thirty-five rows at fifty plantlets with three growing sheets per foot of rack. If six racks can be spaced per foot, then over 32,000 plugs may be grown per square foot using the present invention as compared to 400 in the prior art.

While this invention has been described fully and completely with emphasis on the preferred embodiment, it should be understood that within the scope of the appended claims, the invention may be practiced otherwise and as specifically described and shown herein.

I claim:

1. An enclosure having a floor, walls and roof for growing plants therewithin, comprising:

a track supported above the floor;

a plurality of rack members movably supported by said track;

each of said rack members supporting at least one growing sheet having means for supporting and growing the plants; and means for moving said rack members along said track;

each growing sheet comprising:

a sheet of translucent support material sized to support the growing plants;

a plurality of lengths of second material affixed to said sheet at predetermined locations to form a plurality of rows of growing cells adapted to support and grow the growing plants;

said rows being affixed to said sheet so as to allow areas above said growing cells for the plants to grow; and means for supporting said sheet in a vertical position.

2. The apparatus of claim 1 wherein said cells are formed by heat sealing vertical locations of said lengths of second material and folding and heat sealing a lower peripheral edge of said second material to said sheet.

3. The apparatus of claim 2 wherein said lower peripheral edge is folded evenly outward to avoid restricting a chamber formed by said cell.

4. The apparatus of claim 1 wherein said growing cell includes a weep hole.

5. The apparatus of claim 1 wherein said support material and second material are high density polyethylene.

6. The apparatus of claim 5 wherein said high density polyethylene is Chevron HD 9650.

7. The apparatus of claim 1 wherein said support material and second material are degradable.

8. The apparatus of claim 1 wherein said second material is low density polyethylene.

9. The apparatus of claim 1 wherein said support material and second material are gas permeable, liquid impermeable, and translucent.

10. The apparatus of claim 1 wherein said vertical support means includes a frame having a plurality of supports for supporting a plurality of said sheets.

11. The apparatus of claim 10 wherein said supports are pivotally connected to said frame.

12. An enclosure having a floor, walls and roof for growing plants therewithin, comprising:

a track supported above the floor;

a plurality of rack members movably supported by said track;

each of said rack members supporting at least one growing sheet having means for supporting and growing the plants;

each growing sheet including a sheet of translucent material extending vertically from said rack members and means for moving said rack members along said track;

each of said rack members comprising a frame member that releasably supports at least one growing sheet, and includes top and bottom horizontal bars, side vertical bars, and a center vertical bar.

13. The apparatus of claim 12 further including at least one pair of horizontal support bars, said support bars each releasably supporting said growing sheets.

14. The apparatus of claim 13 wherein said support bars have one end hingedly affixed to one of said side bars or center bar and another end releasably fastened to another one of said side or center bars.

15. An enclosure having a floor, walls and roof for growing plants therewithin, comprising:

a track supported above the floor;

a plurality of rack members movably supported by said track;

each of said rack members supporting at least one translucent growing sheet having means for supporting and growing the plants, such that light can pass through said growing sheet between the plants;

means for moving said rack members along said track; and said track being a closed loop and including an expander section which lengthens the distance between adjacent rack members.

16. The enclosure of claim 15 wherein said expander section includes a spiral thread therearound.

* * * * *